United States Patent
Blaustein et al.

(10) Patent No.: US 7,761,947 B2
(45) Date of Patent: Jul. 27, 2010

(54) COMPLEX MOTION TOOTHBRUSH

(75) Inventors: Lawrence A. Blaustein, Moreland Hills, OH (US); Douglas A. Gall, Westlake, OH (US); Patrick W. Brown, Mantua, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/358,582

(22) Filed: Feb. 21, 2006

(65) Prior Publication Data

US 2006/0137118 A1 Jun. 29, 2006

Related U.S. Application Data

(63) Continuation of application No. 11/200,680, filed on Aug. 10, 2005, now abandoned, which is a continuation of application No. 10/903,222, filed on Jul. 30, 2004, now abandoned, which is a continuation of application No. 10/036,613, filed on Nov. 7, 2001, now abandoned.

(51) Int. Cl.
A61C 17/22 (2006.01)
(52) U.S. Cl. .......................... 15/22.4; 15/22.2
(58) Field of Classification Search .............. 15/22.1, 15/22.2, 22.4, 28, 201
See application file for complete search history.

(56) References Cited

U.S. PATENT DOCUMENTS

| | | | |
|---|---|---|---|
| 793,587 A | 6/1905 | Johnson | |
| 1,212,001 A | 1/1917 | Baxter | |
| 1,255,028 A | 1/1918 | Leonard et al. | |
| 1,392,623 A | 10/1921 | Cheatham | |
| 1,517,320 A | 12/1924 | Stoddart | |
| 1,553,456 A | 9/1925 | Metrakos | |
| 1,557,244 A | 10/1925 | Dominque | |
| 1,896,731 A | 2/1933 | Lippett | |
| 1,981,688 A | 11/1934 | Conti | |
| 1,997,352 A | 4/1935 | Fleet | |
| 2,044,863 A | 6/1936 | Sticht | |
| 2,140,307 A | 12/1938 | Belaschk | |
| 2,172,624 A | 9/1939 | Robert | |
| 2,215,031 A | 9/1940 | Elmore | |

(Continued)

FOREIGN PATENT DOCUMENTS

CA 1082408 7/1980

(Continued)

OTHER PUBLICATIONS

Bader, "Review of Currently Available Battery-Operated Toothbrushes", *Compend. Contin. Educ. Dent.*, vol. 13, No. 12, p. 1162, 1164-1169.

(Continued)

*Primary Examiner*—Laura C Guidotti
(74) *Attorney, Agent, or Firm*—Vladimir Vitenberg; George H. Leal; James C. Vago

(57) ABSTRACT

An electrically driven toothbrush may comprise a shaft comprising a cam. The cam may contact and move a first bristle holder. The shaft may drivingly engage the first bristle the holder. A second bristle holder may be driven by the first bristle holder. The second bristle holder may be driven by an engagement with an element extending from the first bristle holder.

14 Claims, 6 Drawing Sheets

U.S. PATENT DOCUMENTS

| | | | |
|---|---|---|---|
| 2,379,049 A | 6/1945 | Tompkins | |
| 2,435,421 A | 2/1948 | Blair | |
| 2,601,567 A | 6/1952 | Steinberg | |
| 3,103,027 A | 9/1963 | Birch | |
| 3,115,652 A | 12/1963 | Zerbee | |
| 3,129,449 A | 4/1964 | Cyzer | |
| 3,159,859 A | 12/1964 | Rasmussen | |
| 3,160,902 A | 12/1964 | Aymar | |
| 3,178,754 A | 4/1965 | Cleverdon | |
| 3,195,537 A | 7/1965 | Blasi | |
| 3,230,562 A | 1/1966 | Birch | |
| 3,242,516 A * | 3/1966 | Cantor | 15/28 |
| 3,350,737 A | 11/1967 | Makowsky | |
| 3,379,906 A | 4/1968 | Spohr | |
| 3,398,421 A | 8/1968 | Rashbaum | |
| 3,509,874 A | 5/1970 | Stillmann | |
| 3,524,088 A | 8/1970 | Ryckman | |
| 3,538,530 A | 11/1970 | Stemme | |
| 3,577,579 A | 5/1971 | Duve | |
| 3,588,936 A | 6/1971 | Duve | |
| 3,592,188 A | 7/1971 | Barnett | |
| 3,935,869 A | 2/1976 | Reinsch | |
| 3,945,076 A | 3/1976 | Sung | |
| 3,978,852 A | 9/1976 | Annoni | |
| 4,027,348 A | 6/1977 | Flowers et al. | |
| 4,081,876 A | 4/1978 | Pugh | |
| 4,156,620 A | 5/1979 | Clemens | |
| 4,175,299 A | 11/1979 | Teague, Jr. et al. | |
| 4,274,173 A | 6/1981 | Cohen | |
| 4,326,314 A | 4/1982 | Moret et al. | |
| 4,346,492 A | 8/1982 | Solow | |
| 4,397,055 A | 8/1983 | Cuchiara | |
| 4,479,516 A | 10/1984 | Hunter | |
| 4,545,087 A | 10/1985 | Nahum | |
| 4,766,630 A | 8/1988 | Hegemann | |
| 4,791,945 A | 12/1988 | Moriyama | |
| 4,795,347 A | 1/1989 | Maurer | |
| 4,827,550 A | 5/1989 | Graham et al. | |
| 4,845,795 A | 7/1989 | Crawford | |
| 4,845,796 A | 7/1989 | Mosley | |
| 4,894,880 A | 1/1990 | Aznavoorian | |
| 4,974,278 A | 12/1990 | Hommann | |
| 4,989,287 A | 2/1991 | Scherer | |
| 4,995,131 A | 2/1991 | Takeda | |
| 5,033,150 A | 7/1991 | Gross et al. | |
| 5,046,213 A | 9/1991 | Curtis et al. | |
| 5,068,939 A | 12/1991 | Holland | |
| 5,070,567 A | 12/1991 | Holland | |
| 5,077,855 A | 1/1992 | Ambasz | |
| 5,088,145 A | 2/1992 | Whitefield | |
| 5,099,536 A | 3/1992 | Hirabayashi | |
| 5,120,225 A | 6/1992 | Amit | |
| 5,138,734 A * | 8/1992 | Chung | 15/28 |
| D330,286 S | 10/1992 | Curtis et al. | |
| 5,170,525 A | 12/1992 | Cafaro | |
| 5,177,826 A | 1/1993 | Vrignaud et al. | |
| 5,186,627 A | 2/1993 | Amit et al. | |
| D334,473 S | 4/1993 | Volpenhein et al. | |
| 5,226,206 A | 7/1993 | Davidovitz et al. | |
| 5,253,382 A | 10/1993 | Beny | |
| 5,259,083 A | 11/1993 | Stansbury, Jr. | |
| 5,276,932 A | 1/1994 | Byrd | |
| 5,301,381 A | 4/1994 | Klupt | |
| 5,311,633 A | 4/1994 | Herzog et al. | |
| 5,321,866 A | 6/1994 | Klupt | |
| 5,335,389 A | 8/1994 | Curtis et al. | |
| 5,337,435 A | 8/1994 | Krasner et al. | |
| 5,353,460 A | 10/1994 | Bauman | |
| 5,359,747 A | 11/1994 | Amakasu | |
| 5,383,242 A | 1/1995 | Bigler et al. | |
| 5,392,483 A | 2/1995 | Heinzelman et al. | |
| 5,398,366 A | 3/1995 | Bradley | |
| 5,404,608 A | 4/1995 | Hommann | |
| 5,416,942 A | 5/1995 | Baldacci et al. | |
| 5,435,034 A | 7/1995 | Bigler et al. | |
| 5,446,940 A | 9/1995 | Curtis et al. | |
| 5,448,792 A | 9/1995 | Wiedemann et al. | |
| 5,465,444 A | 11/1995 | Bigler et al. | |
| 5,493,747 A | 2/1996 | Inakagata et al. | |
| 5,500,970 A | 3/1996 | Maurer et al. | |
| 5,504,958 A | 4/1996 | Herzog | |
| 5,504,959 A | 4/1996 | Yukawa et al. | |
| 5,504,960 A | 4/1996 | Hommann | |
| 5,504,961 A | 4/1996 | Yang | |
| 5,524,312 A | 6/1996 | Tan et al. | |
| 5,528,786 A | 6/1996 | Porat et al. | |
| 5,577,285 A | 11/1996 | Drossler | |
| 5,617,601 A | 4/1997 | McDougall | |
| 5,617,603 A * | 4/1997 | Mei | 15/22.1 |
| 5,625,916 A | 5/1997 | McDougall | |
| 5,679,991 A | 10/1997 | Wolf | |
| 5,687,442 A | 11/1997 | McLain | |
| 5,727,273 A | 3/1998 | Pai | |
| 5,732,432 A | 3/1998 | Hui | |
| 5,732,433 A | 3/1998 | Göcking et al. | |
| 5,735,011 A | 4/1998 | Asher | |
| 5,738,575 A | 4/1998 | Bock | |
| 5,778,474 A | 7/1998 | Shek | |
| 5,784,742 A | 7/1998 | Giuliani | |
| 5,784,743 A | 7/1998 | Shek | |
| RE35,941 E | 11/1998 | Stansbury, Jr. | |
| 5,836,030 A | 11/1998 | Hazeu et al. | |
| 5,842,244 A | 12/1998 | Hilfinger | |
| 5,842,245 A | 12/1998 | Pai | |
| 5,850,655 A | 12/1998 | Göcking et al. | |
| 5,862,558 A | 1/1999 | Hilfinger et al. | |
| 5,867,856 A | 2/1999 | Herzog | |
| 5,876,206 A | 3/1999 | Maurer | |
| 5,901,397 A | 5/1999 | Hafele | |
| 5,956,797 A | 9/1999 | Wilson | |
| 5,974,613 A | 11/1999 | Herog | |
| 5,974,615 A | 11/1999 | Schwarz-Hartmann et al. | |
| 6,000,083 A | 12/1999 | Blaustein et al. | |
| 6,006,394 A | 12/1999 | Bredall et al. | |
| 6,032,313 A | 3/2000 | Tsang | |
| 6,092,252 A | 7/2000 | Fischer et al. | |
| 6,106,290 A | 8/2000 | Weissman | |
| 6,138,310 A | 10/2000 | Porper et al. | |
| D434,563 S | 12/2000 | Lim et al. | |
| 6,178,579 B1 | 1/2001 | Blaustein et al. | |
| 6,189,693 B1 | 2/2001 | Blaustein et al. | |
| 6,195,828 B1 | 3/2001 | Fritsch | |
| 6,237,178 B1 | 5/2001 | Krammer et al. | |
| 6,308,359 B2 | 10/2001 | Fritsch et al. | |
| 6,311,837 B1 | 11/2001 | Blaustein et al. | |
| 6,314,606 B1 | 11/2001 | Hohlbein | |
| 6,347,425 B1 | 2/2002 | Fattori et al. | |
| 6,360,395 B2 | 3/2002 | Blaustein et al. | |
| 6,371,294 B1 | 4/2002 | Blaustein et al. | |
| 6,421,865 B1 | 7/2002 | McDougall | |
| 6,421,866 B1 | 7/2002 | McDougall | |
| 6,434,773 B1 | 8/2002 | Kuo | |
| 6,446,294 B1 | 9/2002 | Specht | |
| 6,453,498 B1 | 9/2002 | Wu | |
| 6,463,615 B1 | 10/2002 | Gruber et al. | |
| 6,510,575 B2 | 1/2003 | Calabrese | |
| 6,536,066 B2 | 3/2003 | Dickie | |
| 6,546,585 B1 | 4/2003 | Blaustein et al. | |
| 6,564,940 B2 | 5/2003 | Blaustein et al. | |
| 6,574,820 B1 | 6/2003 | Boland | |
| 6,623,698 B2 | 9/2003 | Cox et al. | |
| 6,725,490 B2 | 4/2004 | Blaustein | |
| 6,751,823 B2 | 6/2004 | Biro et al. | |
| 6,760,946 B2 | 7/2004 | Boland | |

| | | |
|---|---|---|
| 6,799,346 B2 | 10/2004 | Jeng et al. |
| 6,889,401 B2 | 5/2005 | Fattori et al. |
| 6,892,412 B2 | 5/2005 | Gatzemeyer et al. |
| 6,892,413 B2 | 5/2005 | Blaustein |
| 6,928,685 B1 | 8/2005 | Blaustein |
| 6,932,216 B2 | 8/2005 | Blaustein et al. |
| 6,944,901 B2 | 9/2005 | Gatzemeyer et al. |
| 6,952,854 B2 | 10/2005 | Blaustein |
| 6,983,507 B2 | 1/2006 | McDougall |
| 7,124,461 B2 | 10/2006 | Blaustein |
| 7,140,059 B2 | 11/2006 | Scherl |
| 7,150,061 B2 | 12/2006 | Kwong |
| 7,162,764 B2 | 1/2007 | Drossler et al. |
| 7,225,494 B2 | 6/2007 | Chan et al. |
| 7,258,747 B2 | 8/2007 | Vago et al. |
| 7,302,726 B2 | 12/2007 | Braun |
| 7,340,794 B2 | 3/2008 | Gall |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan |
| 7,430,777 B2 | 10/2008 | Scherl |
| 7,430,778 B2 | 10/2008 | Gatzemeyer et al. |
| 7,448,107 B2 | 11/2008 | Boland |
| 7,451,514 B2 | 11/2008 | Blaustein |
| 7,520,016 B2 | 4/2009 | Kressner |
| 7,552,497 B2 | 6/2009 | Gatzemeyer et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0059685 A1 | 5/2002 | Paffrath |
| 2002/0078514 A1 | 6/2002 | Blaustein et al. |
| 2002/0129454 A1 | 9/2002 | Hilscher et al. |
| 2002/0138926 A1 | 10/2002 | Brown, Jr. |
| 2002/0152564 A1 | 10/2002 | Blaustein et al. |
| 2002/0162180 A1 | 11/2002 | Blaustein et al. |
| 2003/0066145 A1* | 4/2003 | Prineppi ............... 15/22.1 |
| 2003/0074751 A1* | 4/2003 | Wu ........................ 15/22.1 |
| 2003/0084525 A1 | 5/2003 | Blaustein et al. |
| 2003/0084526 A1 | 5/2003 | Gall |
| 2003/0084528 A1 | 5/2003 | Chan |
| 2003/0140435 A1 | 7/2003 | Eliav et al. |
| 2003/0140437 A1 | 7/2003 | Eliav et al. |
| 2003/0154567 A1 | 8/2003 | Drossler et al. |
| 2003/0163881 A1 | 9/2003 | Driesen et al. |
| 2003/0163882 A1 | 9/2003 | Blaustein |
| 2003/0182746 A1 | 10/2003 | Fattori et al. |
| 2003/0196283 A1 | 10/2003 | Eliav et al. |
| 2003/0213075 A1 | 11/2003 | Hui et al. |
| 2003/0226223 A1 | 12/2003 | Chan et al. |
| 2004/0045105 A1 | 2/2004 | Eliav et al. |
| 2004/0060134 A1 | 4/2004 | Eliav et al. |
| 2004/0060135 A1 | 4/2004 | Gatzemeyer et al. |
| 2004/0060136 A1 | 4/2004 | Gatzemeyer et al. |
| 2004/0060137 A1 | 4/2004 | Eliav |
| 2004/0074026 A1 | 4/2004 | Blaustein et al. |
| 2004/0083566 A1 | 5/2004 | Blaustein |
| 2004/0088806 A1 | 5/2004 | DePuydt et al. |
| 2004/0088807 A1 | 5/2004 | Blaustein et al. |
| 2004/0143917 A1 | 7/2004 | Ek |
| 2004/0168272 A1 | 9/2004 | Prineppi |
| 2004/0177458 A1 | 9/2004 | Chan et al. |
| 2004/0177462 A1 | 9/2004 | Brown, Jr. |
| 2005/0000043 A1 | 1/2005 | Chan et al. |
| 2005/0000045 A1 | 1/2005 | Blaustein |
| 2005/0091771 A1 | 5/2005 | Blaustein |
| 2005/0102776 A1 | 5/2005 | Mathur |
| 2005/0155167 A1 | 7/2005 | Gall |
| 2005/0268409 A1 | 12/2005 | Blaustein |
| 2005/0279974 A1 | 12/2005 | Blaustein et al. |
| 2006/0032006 A1 | 2/2006 | Gall |
| 2006/0048314 A1 | 3/2006 | Kressner |
| 2006/0048315 A1 | 3/2006 | Chan |
| 2006/0137118 A1 | 6/2006 | Blaustein |
| 2006/0254006 A1 | 11/2006 | Blaustein |
| 2006/0254007 A1 | 11/2006 | Banning |
| 2007/0251033 A1 | 11/2007 | Gall |
| 2008/0010761 A1 | 1/2008 | Blaustein |
| 2008/0016633 A1 | 1/2008 | Blaustein |
| 2008/0078040 A1 | 4/2008 | Braun |
| 2009/0106923 A1 | 4/2009 | Boland |

FOREIGN PATENT DOCUMENTS

| | | |
|---|---|---|
| CA | 2141569 | 2/1994 |
| CH | 324623 | 11/1957 |
| CH | 358408 | 1/1962 |
| CN | 2681701 Y | 6/1954 |
| CN | 2236827 Y | 7/1996 |
| CN | 2271353 Y | 10/1997 |
| CN | 2271352 Y | 12/1997 |
| CN | 2274947 Y | 2/1998 |
| CN | 330411 | 4/1998 |
| CN | 1187341 A | 7/1998 |
| CN | 2324988 | 6/1999 |
| CN | 2324988 Y | 6/1999 |
| CN | 2558353 | 7/2003 |
| DE | 8426426.8 | 3/1985 |
| DE | 3406112 | 8/1985 |
| DE | 3544256 | 8/1987 |
| DE | 4003305 | 8/1991 |
| DE | 29600236 | 4/1996 |
| DE | 29613608 | 11/1996 |
| DE | 29618755 | 3/1997 |
| DE | 19701964 | 7/1998 |
| DE | 2736286 | 12/1998 |
| DE | 298 09 977 | 2/1999 |
| DE | 19802904 | 7/1999 |
| DE | 19803311 | 8/1999 |
| EP | 259648 | 3/1988 |
| EP | 0 208 401 B1 | 5/1991 |
| EP | 0 254 397 | 7/1991 |
| EP | 0 546 203 B1 | 6/1993 |
| EP | 0 520 985 B1 | 8/1997 |
| EP | 1 053 721 B1 | 11/2000 |
| EP | 1059049 | 12/2000 |
| EP | 1132057 | 9/2001 |
| GB | 1583558 | 1/1981 |
| GB | 2237505 | 8/1991 |
| GB | 2247297 | 2/1992 |
| GB | 2290224 | 12/1995 |
| GB | 2319170 | 5/1998 |
| JP | 40-8743 | 8/1965 |
| JP | 57-89810 | 6/1982 |
| JP | 2-19241 | 2/1990 |
| JP | 02-218309 | 8/1990 |
| JP | 03-001895 | 1/1991 |
| JP | 4-133733 | 7/1991 |
| JP | 05-146313 | 6/1993 |
| JP | 05-146314 | 6/1993 |
| JP | 5-269023 | 10/1993 |
| JP | 6-47298 | 2/1994 |
| JP | 06-189822 | 7/1994 |
| JP | 7-116020 | 5/1995 |
| JP | 7-116021 | 5/1995 |
| JP | 7-116023 | 5/1995 |
| JP | 7-116024 | 5/1995 |
| JP | 7-93892 | 10/1995 |
| JP | 2511226 | 7/1996 |
| JP | 8-322641 | 10/1996 |
| JP | 10-066704 | 3/1998 |
| JP | 2804940 | 7/1998 |
| JP | 2811246 | 10/1998 |
| JP | 11-505742 | 5/1999 |

| | | |
|---|---|---|
| KR | 1984-0004668 | 9/1984 |
| KR | 1986-0001137 | 6/1986 |
| KR | 91-700015 | 3/1991 |
| KR | 1994-0013418 | 7/1994 |
| KR | 1995-0002814 | 2/1995 |
| KR | 1995-0010820 | 5/1995 |
| KR | 1997-0000408 | 1/1997 |
| KR | 1997-0000409 | 1/1997 |
| KR | 143460 | 4/1998 |
| KR | 100143460 B | 4/1998 |
| TW | 135303 | 5/1905 |
| TW | 257968 | 6/1905 |
| TW | 154730 | 3/1979 |
| TW | 164493 | 7/1979 |
| TW | 200663 | 5/1981 |
| TW | 248031 | 12/1982 |
| TW | 274724 | 4/1984 |
| TW | 137856 | 12/1988 |
| TW | 256049 | 1/1993 |
| TW | 238504 | 6/1993 |
| TW | 212909 | 9/1993 |
| TW | 253174 | 7/1994 |
| TW | 294031 | 11/1994 |
| TW | 239963 | 2/1995 |
| TW | 239964 | 2/1995 |
| TW | 311444 | 12/1996 |
| TW | 309753 | 7/1997 |
| TW | 330411 | 4/1998 |
| TW | 334345 | 6/1998 |
| TW | 406557 | 9/2000 |
| WO | WO 99/23910 | 5/1999 |
| WO | WO 01/06946 | 2/2001 |
| WO | WO 01/06947 | 2/2001 |
| WO | WO 01/21094 | 3/2001 |
| WO | WO 01/43586 | 6/2001 |
| WO | WO 02/102187 A1 | 12/2002 |
| WO | WO 03/020159 | 3/2003 |
| WO | WO 03/039397 | 5/2003 |
| WO | WO 2004/045448 A1 | 6/2004 |

OTHER PUBLICATIONS

U.S. Appl. No. 10/237,902, Filed Sep. 9, 2002 entitled Topper for Power Toothbrush and Method for Forming the Same, all pages.
Photographs of electric toothbrush of BioBrush Industries (22 photographs).
PCT International Search report dated Jun. 3, 2003.
Office Action for U.S. Appl. No. 10/903,222; P&G; dated Apr. 11, 2005.
Office Action for U.S. Appl. No. 10/903,222; P&G; dated Oct. 19, 2004.
Office Action for U.S. Appl. No. 11/200,680; P&G; dated Sep. 22, 2005.
Office Action for U.S. Appl. No. 10/676,955; P&G; dated Jan. 24, 2005.
Office Action for U.S. Appl. No. 10/676,955; P&G; dated Jul. 12, 2005.
Office Action for U.S. Appl. No. 10/676,955; P&G; dated Jul. 29, 2004.
Office Action for U.S. Appl. No. 10/927,845; P&G; dated Dec. 28, 2004.
Office Action for U.S. Appl. No. 10/929,288; P&G; dated Mar. 18, 2005.
Office Action for U.S. Appl. No. 10/929,288; P&G; dated Aug. 24, 2005.
Office Action for U.S. Appl. No.11/514,742; P&G; dated Mar. 17, 2008.
Office Action for U.S. Appl. No. 11/514,742; P&G; dated Aug. 17, 2007.
Office Action for U.S. Appl. No. 11/514,742; P&G; dated Apr. 10, 2008.
Office Action for U.S. Appl. No. 11/006,972; P&G; dated Mar. 24, 2005.
Office Action for U.S. Appl. No. 10/896,540; P&G; dated Oct. 4, 2004.
Office Action for U.S. Appl. No. 11/414,908; P&G; dated May 23, 2007.
Office Action for U.S. Appl. No. 11/801,000; P&G; dated Jun. 20, 2008.
Office Action for U.S. Appl. No. 11/801,000; P&G; dated Sep. 26, 2008.
Office Action for U.S. Appl. No. 11/801,000; P&GC; dated Oct. 26, 2007.
Office Action for U.S. Appl. No. 11/801,000; P&G; dated Dec. 5, 2008.
Office Action for U.S. Appl. No. 10/308,959; P&G; dated Feb. 16, 2006.
Advisory Action for U.S. Appl. No. 11/486,725; P&G; dated Jan. 28, 2008.
Office Action for U.S. Appl. No. 11/486,725; P&G; dated Jan. 28, 2009.
Office Action for U.S. Appl. No. 11/486,725; P&G; dated Jan. 29, 2007.
Office Action for U.S. Appl. No. 11/486,725; P&G; dated Apr. 10, 2008.
Office Action for U.S. Appl. No. 11/486,725; P&G; dated Aug. 13, 2007.
Office Action for U.S. Appl. No. 11/893,469; P&G; dated Oct. 14, 2008.
Office Action for U.S. Appl. No. 11/893,469; P&G; dated Dec. 18, 2008.
Office Action for U.S. Appl. No. 11/410,808; P&G; dated Feb. 15, 2007.
Office Action for U.S. Appl. No. 11/410,808; P&G; dated Jul. 17, 2007.
Office Action for U.S. Appl. No. 11/015,111; P&G; dated Nov. 24, 2008.
Office Action for U.S. Appl. No. 11/220,219; P&G; dated Oct. 20, 2008.
Office Action for U.S. Appl. No. 10/367,373; dated Mar. 9, 2004.
Office Action for U.S. Appl. No. 09/425,423; P&G; dated Jan. 31, 2002.
Office Action for U.S. Appl. No. 09/425,423; P&G; dated Aug. 14, 2002.
Office Action for U.S. Appl. No. 10/331,799; P&G; dated Apr. 19, 2005.
Office Action for U.S. Appl. No. 10/331,799; P&G; dated Oct. 14, 2005.
Office Action for U.S. Appl. No. 10/331,799; P&G; dated Feb. 23, 2006.
Office Action for U.S. Appl. No. 09/993,167; P&G; dated Dec. 18, 2002.
Office Action for U.S. Appl. No. 09/993,167; P&G; dated Apr. 16, 2003.
Office Action for U.S. Appl. No. 11/295,907; P&G; dated Jun. 5, 2009.

* cited by examiner

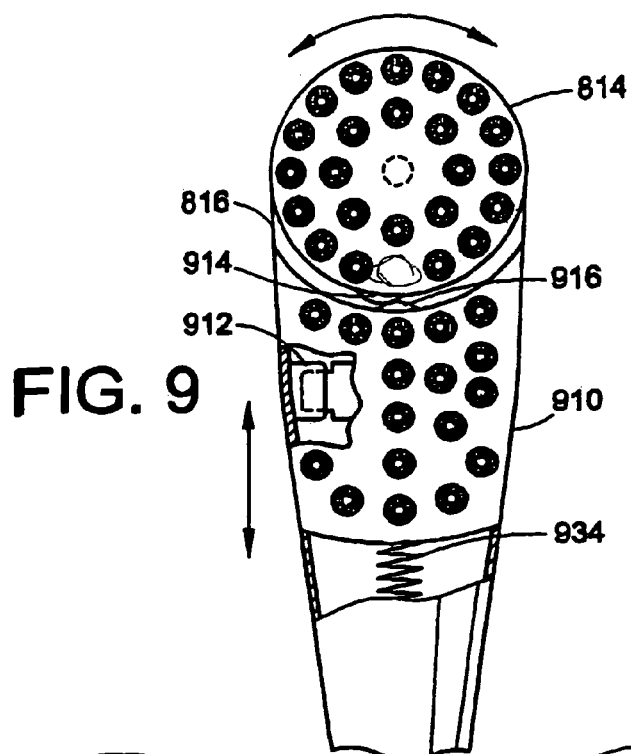
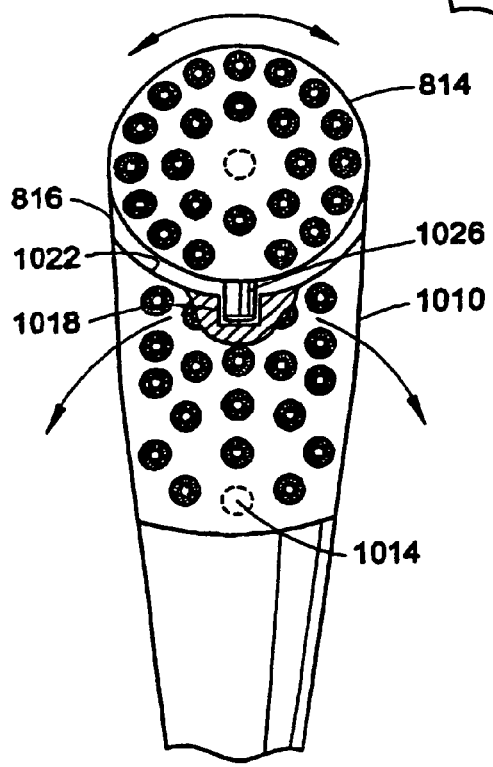
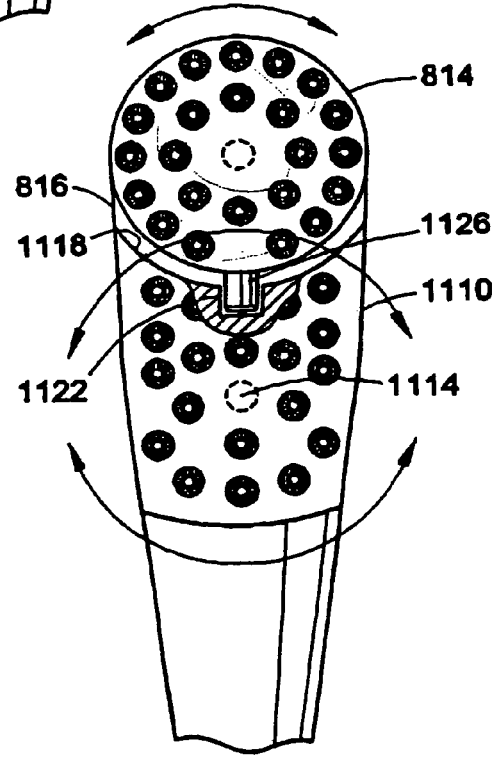
FIG. 9
FIG. 10
FIG. 11

COMPLEX MOTION TOOTHBRUSH

CROSS REFERENCES TO RELATED APPLICATIONS

This application is a continuation of application Ser. No. 11/200,680, filed Aug. 10, 2005, now abandoned which is a continuation of application Ser. No. 10/903,222, filed Jul. 30, 2004, now abandoned which is a continuation of application Ser. No. 10/036,613, filed Nov. 7, 2001, now abandoned the substances of which is incorporated herein by reference.

FIELD OF THE INVENTION

The invention is related to the art of toothbrushes

DESCRIPTION OF RELATED ART

The invention relates more particularly to electrically driven toothbrushes in which brush bristles are arranged to be moved relative to the toothbrush handle. There are many examples of such toothbrushes including the disclosure in 1939 of rotary driven bristles in U.S. Pat. No. 2,215,031, A similar rotational drive arrangement is also shown in U.S. Pat. No. 4,845,795, U.S. Pat. No. 4,156,620 explains how a rotational motor drive is converted into reciprocal linear motion to drive the bristles rotationally clockwise and counterclockwise, U.S. Pat. No. 3,577,579 discloses a toothbrush in which a toothbrush head is moved in relation to a brush holder so that all the bristles mounted in the brush head move together sideways and backwards and forwards relative to the holder. U.S. Pat. No. 5,625,916 discloses a toothbrush with a single bristle holder. The bristle holder is driven to vibrate in a rotational manner about a shaft. U.S. Pat. No. 5,617,603, the substance of which is hereby incorporated by reference, discloses a toothbrush with two bristle holders interconnected by a separate swing bar. The swing bar is mounted on a pivot pin. The two bristle holders include recesses, which receive ball ends of the swing bar.

The drive mechanisms and brush motions disclosed in these references range from the relatively simple to the relatively complex. The complex disclosures describe toothbrushes that provide elaborate brushing motions. However, the toothbrushes are far too complicated and involve too many moving parts to be a practical brushing solution in many applications. The simpler of the disclosed toothbrushes, provide only one brushing action. These singular brushing actions may provide adequate brushing action in some applications. However, they may also be inadequate in other brushing situations. For example, they may not adequately clean spaces between teeth.

It is desirable therefore to provide a toothbrush that is simple to manufacture, having few moving parts, while providing a plurality of cleaning or brushing actions for accomplishing a plurality of teeth cleaning tasks.

BRIEF SUMMARY OF THE INVENTION

One embodiment of the new toothbrush includes a handle at a first end of the toothbrush and a head at a second end of the toothbrush. The toothbrush also includes a rotatable shaft extending from the handle to the head and having a first longitudinal central axis, a first bristle holder mounted with a first pivot or hinge to the head and associated with a remote end cam or gear tooth of the shaft, the remote end, cam or gear tooth of the shaft being received in a slot of the first bristle holder for driving the first bristle holder in pivoting vibratory movement. Additionally, the toothbrush also includes a second bristle holder movably mounted to the head section and drivingly engaged by a rigidly mounted portion of the first bristle holder.

Another embodiment of the electric toothbrush includes a shaft, the shaft including a cam or gear tooth at a remote-most end of the shaft, a motor operative to rotate the shaft, a first brush section operatively coupled to the cam or gear tooth for being driven in a first motion and, a second brush section longitudinally separated from the first brush section and driven in a second motion by a rigid element of the first brush section.

One advantage of the present invention resides in complementary cleaning motions provided respectively by the first and second bristle holders Another advantage of the present invention is that complementary cleaning motions are provided in a simple and economical toothbrush.

Still other advantages of the present invention will become apparent to those skilled in the art upon a reading and understanding of the detail description below.

BRIEF DESCRIPTION OF THE SEVERAL VIEWS OF THE DRAWINGS

The invention may take form in various components and arrangements of components, and in various procedures and arrangements of procedures. The drawings are only for purposes of illustrating preferred embodiments, they are not to scale, and are not to be construed as limiting the invention.

FIG. 9 is a bottom view, in partial section, of a first embodiment of a head portion of the enhanced toothbrush of FIG.8.

FIG. 10 is a bottom view, in partial section, of a second embodiment of a head portion of the enhanced toothbrush of FIG.8.

FIG. 11 is a bottom view, in partial section, of a third embodiment of a head portion of the enhanced toothbrush of FIG.8.

DETAILED DESCRIPTION OF THE INVENTION

Figure 1:
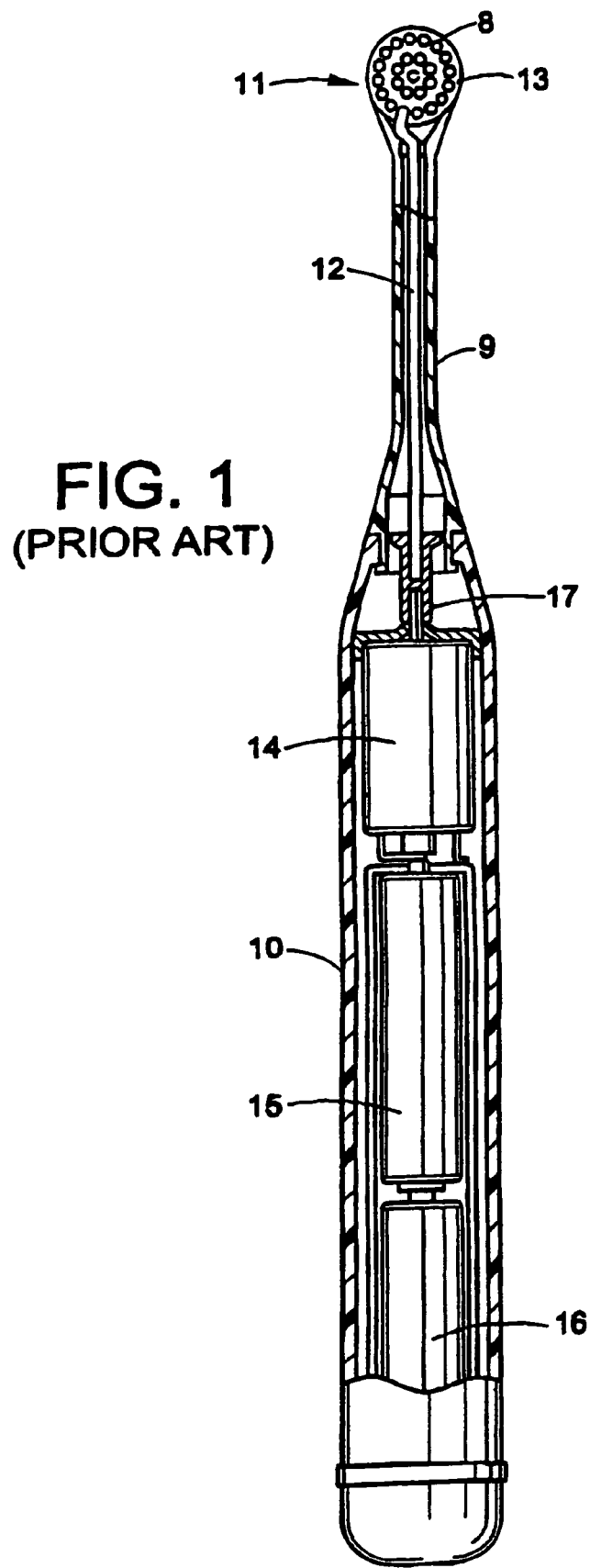
FIG. 1 is a sectional bottom view of a prior art toothbrush.
Figure 4:
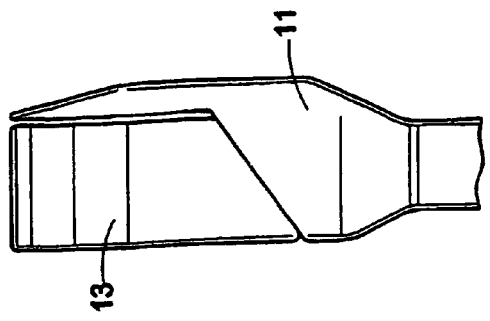
FIG. 4 is an opposite side view of FIG. 2.
Figure 7:
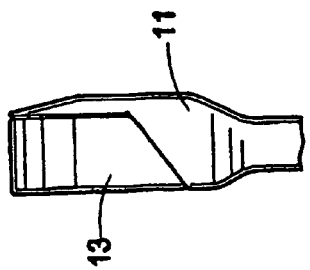
FIGS. 5, 6 and 7 are respectively the same views as FIGS. 2, 3 and 4 of a different prior art toothbrush and to a different scale.

Referring to the drawings, in FIG. 1 the toothbrush comprises a handle portion 10 at a first end of the toothbrush, a head section 11 at a second end of the toothbrush, a neck 9 extending therebetween, a rotatable shaft 12 extending from the handle to the head, and a generally circular bristle holder 13 having a plurality of bristle tufts embedded therein, wherein each tuft 8 comprises a plurality of bristles. The handle provides compartments for holding an electric motor 14 and two batteries 15 and 16, although a rechargeable power source can be substituted for the batteries 15 and 16. A shaft coupling 17 is arranged to grip one end of the shaft 12 and allow the shaft to be pulled out for cleaning or replacement as will be described below.

Figure 2:
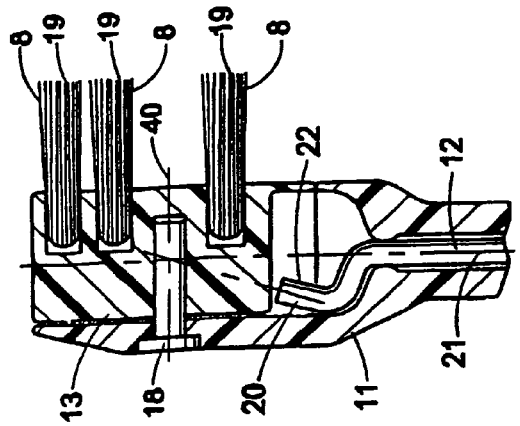
FIG. 2 shows a cross-sectional side view of part of the prior art toothbrush.

The head 11, as is better seen in FIG. 2, supports a post 18, which provides a rotational or oscillatory pivot axis 40 for the bristle holder 13. Bristles 19 are shown for illustrative purposes only in FIG. 2. The shaft 12 has an integrally formed remote-most end, gear tooth or gear tooth 20 that is off-set from a central longitudinal axis 21 of the shaft. The remote-most end, gear tooth or cam 20 fits into a slot 22 (see FIG. 3) formed in a side of the bristle holder 13. It will be noted that the end 20 points towards an intersection of the first axis 21 and the pivot axis 40 of the post 18. In one embodiment, the post is arranged so that the pivot axis 40 is substantially perpendicular to the central longitudinal axis 21 of the shaft. The pivot axis 40 is also substantially parallel to the central longitudinal axis 21 of the shaft. The pivot axis 40 is also substantially parallel to the direction in which the bristles 19 extend. While this arrangement is preferred, it is contemplated that the post 18 can be arranged differently. For example, the post 18 might be angled so that the pivot axis 40 is not substantially perpendicular to the longitudinal axis 21 of the shat but rather forms an acute angel therewith in order to provide a wobbling or swiveling action about the pivot axis 40. When the shaft 12 is rotated by the motor 14, the remote end, gear tooth or cam 20 describes a circle about the shaft 12 and drivingly engages the slot 22 to cause the bristle holder 13 to vibrate or oscillate about the pivot axis of the bristle holder 13. In this regard the remote end is formed into a remote gear tooth or cam 20. As may be seen in FIG. 3, slot 22 is closed-ended and extends radially inward from the outer circumference of the holder to less than the distance to the center of the holder and between adjacent pairs of bristle holes. Thus, the bristle holder 13 pivots, oscillates, or rotates forwards and backwards about the center of the post 18. Such movement provides a first relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

Figure 5:
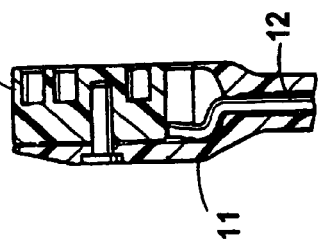
Figure 8:
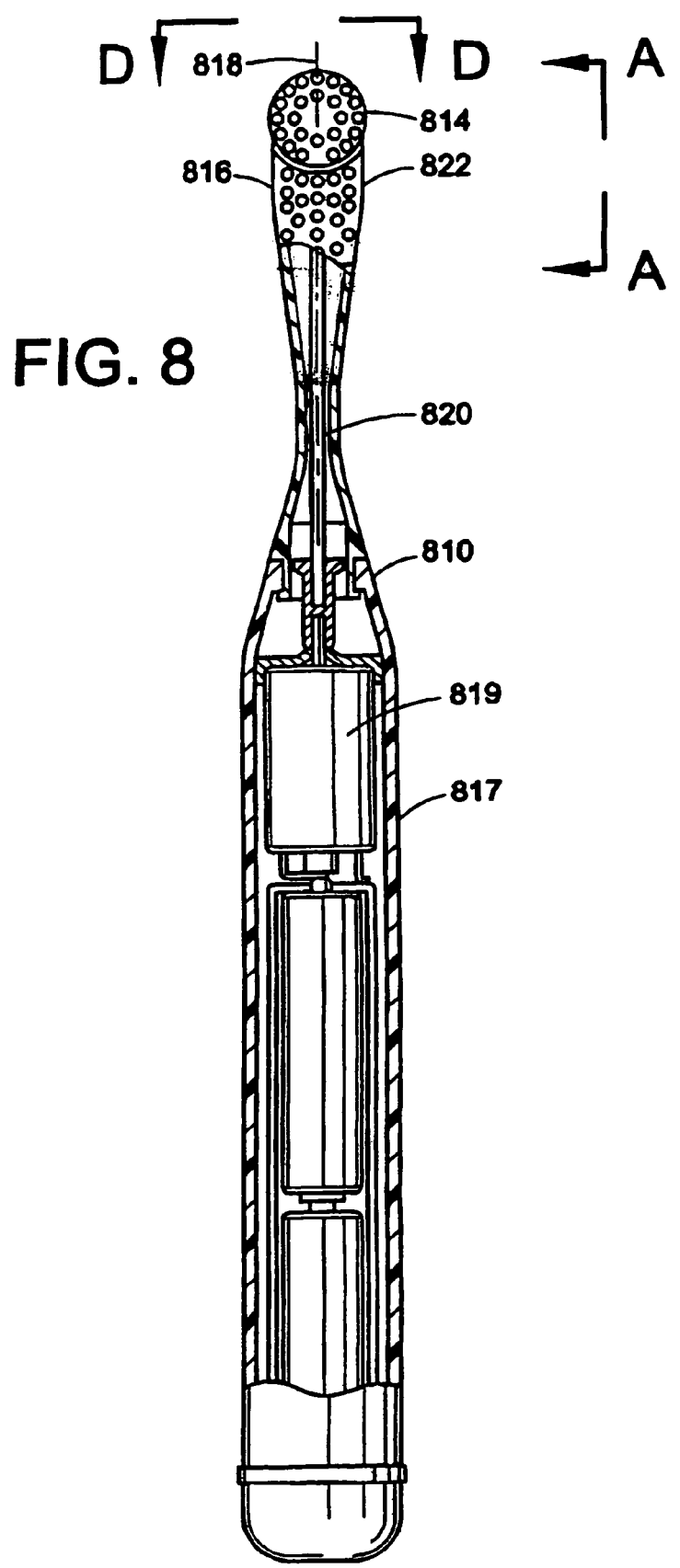
FIG. 8 is a bottom view of an enhanced toothbrush in partial section.

Preferably, the motor 14 runs at around 6000 rpm. Where desired, the motor can run at other speeds or be arranged to run at two or more speeds, selectable by the user. FIG. 1 shows a toothbrush where the holder 13 vibrates, oscillates or rotates through an angle of 30 degrees. In FIG. 2, the angle is 35 degrees and in FIG. 5 the angle is 15 degrees. It will therefore be appreciated that the rotational angle can be chosen by fitting different shafts 12 and that the same bristle holder can be used for all angles.

Figure 3:
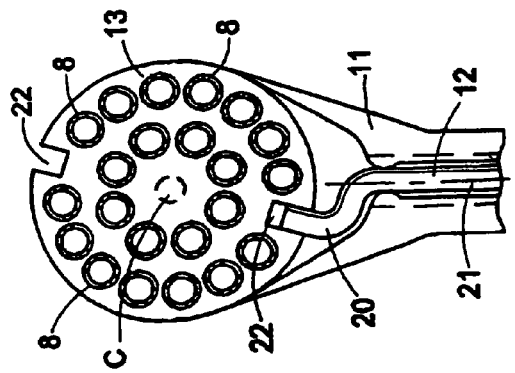
FIG. 3 is a sectional bottom view of FIG. 2.
Figure 6:
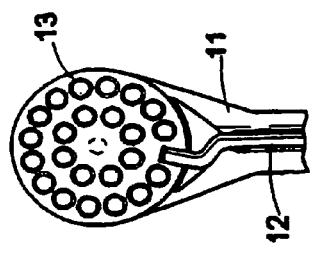

Each bristle holder 13 may be provided with more than one slot 22 as may be seen in FIG. 3, opposite each other so as to be better balanced or so that different slots can be used if the one slot wears or if the bristles wear unevenly in use. In other words, the holder 13 can then be set up in two or more rotational positions. The holder 13 is preferable easily removable from the head 11, by being spring clipped to the post 18, for example. Such removal allows better cleaning and storing in a hygienic container perhaps and also enables the shaft 12 to be readily withdrawn and replaced when required.

The described shafts 12 are preferably integrally formed, i.e., a single length of a thin rod and shaped as shown. However, it is possible to arrange for the remote end or cam 20 to be separately formed or provided and fixed to a part of the shaft. Such a separate part can be a brush having a central axis coinciding with the axis 21 of the shaft and an off-center driving post. The driving post then takes up the position and function of the remote cam 20. Thus, the driving post and the slot 22 then form the driving engagement between the shaft and the holder 13 and so the driving post can be regarded as the remote cam of the shaft.

It is also possible, but not usually so convenient, in some embodiments of the invention to arrange for the holder 13 to be hingedly pivoted at one side, for example opposite the shaft. In such a case, bristles mounted nearer the hinged pivot will not actually move as much as bristles at the side next to the shaft but they will still vibrate significantly.

It will also be appreciated that whether pivoted to rotate or to hinge, the bristle holder 13 need not be circular. However, a circular holder 13 is normally preferred so that its rotational position can be changed when desired, as mentioned above.

While the above-described shaft arrangement is preferred, it is contemplated that other shaft arrangements can be used with the present invention. For example, the arrangement described in U.S. Pat. No. 5,732,432, the substance of which is incorporated herein by reference, might be substituted to accommodate mechanical misalignments of the shaft and mechanical strain during use. Further, the head 11 might be provided in a form in which it can be readily detached from the handle 10. This could be accomplished using, coupling arrangements for the shaft and body portion of the head. Such arrangements are known in the art. For example, the head and handle portions can include mating slots, spring clips, and protrusions and/or locking or securing tabs and grooves. The shaft can be divided into two sections, each section including a coupling element. For example, the coupling is achieved with a keyed arrangement. For instance, coupling elements can include male and female mating splines affixed to respective shaft section ends, or as shown in U.S. Pat. No. 5,617,601, the substance of which is incorporated herein by reference. Further, the slot 22 might be replaced by a wobble plate, such as described in U.S. Pat. No. 5,764,743, the substance of which is incorporated herein by reference.

With additional reference now to FIG. 8-FIG. 15, embodiments of an enhanced electric toothbrush 810 include a first bristle holder 814 similar to the bristle holder 13 described above. The enhanced toothbrush 810 has a head portion 816 and a body or handle portion 817. Of course, the enhanced toothbrush includes a motor 819 and batteries for powering the motor. The head portion 816 has a longitudinal axis 818. The first bristle holder 814 is illustrated as circular. However, other shape bristle holders are contemplated and within the scope of the invention. The first bristle holder 814 includes at least one slot described above for receiving a remote most end or cam of a driving shaft 820 as described in reference to FIG. 1-FIG. 7. The remote-most cam (see FIG. 3) of the driving shaft is bent or offset from a central longitudinal axis 21 (see FIG. 3) of the driving shaft 820 as described above. In short, with regard to the construction and operation of the shaft 820 in relation to the first bristle holder 814, the enhanced toothbrush 810 is similar to the toothbrush described in reference to FIG. 1-FIG. 7. However, embodiments of the enhanced electric toothbrush 810 also include second bristle holders, such as second bristle holder 822. While it is desirable to locate the second bristle holder directly adjacent the first bristle holder, it is contemplated that a gap may be provided between the first and second bristle holders. In addition, the space between the movable first and second bristle holders might be filled with stationary or fixed bristles which are embedded in fixed or stationary third bristle holder (not shown) which forms part of the toothbrush head. In many embodiments of the enhanced electric toothbrush the second bristle holders are movable and separately associated with, and separately driven by, a driving shaft such as the driving shaft 820. The movable second bristle holders are movable in directions and/or manners that are different and distinct from whichever of the rotary or hingedly pivoted vibratory movements, described in reference to FIG. 1-FIG. 7, is used in the particular embodiment.

For example, referring to FIG. 9, a second bristle holder 910 is movably mounted in slots 912 in the toothbrush head 816 and driven in a vibratory, longitudinal motion by the motion of the first bristle holder 814. For example, the first bristle holder 814 includes a cam 914. The second bristle holder includes a cam follower 916. The cam 914 and cam follower 916 are generally disposed in opposing relation. Additionally, depending on the position of the first bristle holder 814, the cam 914 and cam follower 916 can be in an engaged relation. The cam and cam follower 914, 916 can comprise molded protrusions on the first 814 and second 910 bristle holders respectively. The cam and cam follower 914, 916 are rigidly mounted to or within the first 814 and second 910 bristle holders. That is to say, the cam and cam follower 914, 916 do not move significantly with regard to their respective bristle holders. Therefore the cam and cam follower 914, 916 do not constitute additional moving parts. As the motor 819 of the enhanced toothbrush 810 rotates the shaft 820, a remote-most cam of the shaft 820 (not shown, but similar to 20 of FIG. 3) drives the first bristle holder into rotational vibratory motion as described above in reference to FIG. 1-FIG. 7. As the first bristle holder vibrates or oscillates the first cam 914 comes into contact with a surface of the second cam or cam follower 916 and drives the cam follower 916, and therefore, the second bristle holder in a longitudinal direction along the longitudinal axis 818 of the head portion 816. As the shaft 918 continues to rotate, the first cam 914 becomes disengaged with the cam follower 916. A resilient biasing member such as a spring 934, lodged or mounted, for example, between a wall of the head portion 816 and a surface of the second bristle holder 910, urges the second bristle holder 910 back toward the first bristle holder 814. As this back and forth or up and down motion (relative to the figure) is repeated (as the shaft 820 continues to rotate), a brushing motion is provided that is distinct from and complimentary to the circular motion provided by the first bristle holder 814.

Referring to FIG. 10, in a second embodiment of the enhanced toothbrush 810 a second bristle holder 1010 is movably mounted the toothbrush head 816 and driven in a vibratory, swinging, oscillating or pivoting motion about a hinge or pivot 1014, by the first bristle holder 814. The second bristle holder 1010 is longitudinally spaced from the first bristle holder 814. A first side 1018 of the second bristle holder 1010 faces the first bristle holder 814. The first side 1018 includes a slot 1022. The pivot or hinge 1014 is offset from a center of the second bristle holder. For example, the pivot 1014 is located at a side spaced, or remote from, the first side 1018. A pin 1026 interconnects the first, bristle holder 814 with the second bristle holder 1010. Preferably, the pin 1026 is molded into, and unitary with, the first bristle holder 814. The pin 1026 is rigidly mounted to or within the first 814 holder. That is to say, the pin 1026 does not move significantly with respect to the first bristle holder. Therefore, the pin 1026 does not constitute an additional moving part. The pin 1026 is received in the slot 1022 in the second bristle holder 1010. The slot 1022 is sized to allow the pin 1018 to slide and pivot relative to the slot and to engage portions of walls of the slot. As the motor 819 of the enhanced toothbrush 810 rotates the shaft 820, a remote-most end or cam (not shown, but similar to 20 of FIG. 3) of the shaft 820 drives the first bristle holder 814 into rotational vibratory motion as described above in reference to FIG. 1-FIG. 7. As the first bristle holder 814, vibrates or oscillates, the pin 1018 associated therewith is sweeps out and arc. As the pin 1026 sweeps out the arc in a first direction, the pin 1026 engages a first wall of the slot 1022 and urges the first wall, and therefore, the second bristle holder, to move in the first direction. Since the movement of the second bristle holder is constrained by the hinge or pivot 1014, the second bristle holder 1010 is made to swing about the pivot in the first direction. As the shaft 820 continues to rotate, the first bristle holder is made to move in a second direction. Therefore the pin 1026 is made to sweep out an arc in the second direction. As the pin 1026 sweeps out the arc in the second direction, the pin 1026 engages a second wall of the slot 1022 and urges the second wall, and therefore the second bristle holder, to move in the second direction. Since the movement of the second bristle holder is constrained by the hinge or pivot 1014, the second bristle holder 1010 is made to swing about the pivot in the second direction. As this swinging or pivoting motion is repeated (as the shaft 818 continues to rotate), a brushing motion is provided that is complimentary to that provided by the first bristle holder 814. For example, as the first bristle holder rotates clockwise, the second bristle holder pivots in a complimentary counter clockwise direction.

Referring to FIG. 11, in a third embodiment of the enhanced toothbrush 810 a second bristle holder 1110 is movably mounted the toothbrush head 816 and driven in a vibratory, swinging, oscillating or pivoting motion about a pivot 1114, by the first bristle holder 814. The second bristle holder 1110 is longitudinally spaced from the first bristle holder 814. A first side 1118 of the second bristle holder 1110 faces the first bristle holder 814. The first side 1118 includes a slot 1122. The pivot 1114 is centrally located within the second bristle holder. A pin 1126 interconnects the first bristle holder 814 with the second bristle holder 1110. Preferably, the pin 1126 is molded into, and unitary with, the first bristle holder 814. The pin 1126 is rigidly mounted to or within the first bristle holder 814. That is to say, the pin 1126 does not move significantly with respect to the first bristle holder 814. Therefore, the pin 1126 does not constitute an additional moving part. The pin 1126 is received in the slot 1122 in the second bristle holder 1110. The slot 1122 is sized to allow the pin 1126 to slide and pivot relative to the slot and to engage portions of walls of the slot 1122. As the motor 819 of the enhanced toothbrush 810 rotates the shaft 820, a remote-most cam (not shown, but similar to 20 of FIG. 3) of the shaft 820 drives the first bristle holder into rotational or pivotal vibratory motion as described above in reference to FIG. 1-FIG. 7. As the first bristle holder 814 vibrates, the pin 1118 associated therewith is sweeps out an arc. As the pin 1126 sweeps out the arc in a first direction, the pin 1126 engages a first wall of the slot 1122 and urges the first wall, and therefore the second bristle holder to move in the first direction. Since the movement of the second bristle holder is constrained by the pivot 1114, the second bristle holder 1110 is made to swing or rotate about the pivot 1114 in the first direction. As the shaft 820 continues to rotate, the first bristle holder is made to move in a second direction. Therefore the pin 1126 is made to sweep out an arc in the second direction. As the pin 1126 sweeps out the arc in the second direction, the pin 1126 engages a second wall of the slot 1122 and urges the second wall, and therefore the second bristle holder 1110 to move in the second direction. Since the movement of the second bristle holder is constrained by the pivot 1114, the second bristle holder 1110 is made to swing or rotate about the pivot in the second direction. As this swinging or pivoting motion is repeated (as the shaft 820 continues to rotate), a brushing motion is provided that is complimentary to that provided by the first bristle holder 814. For example, as the first bristle holder moves clockwise, the second bristle holder moves in a complimentary counter clockwise direction.

Figure 12:
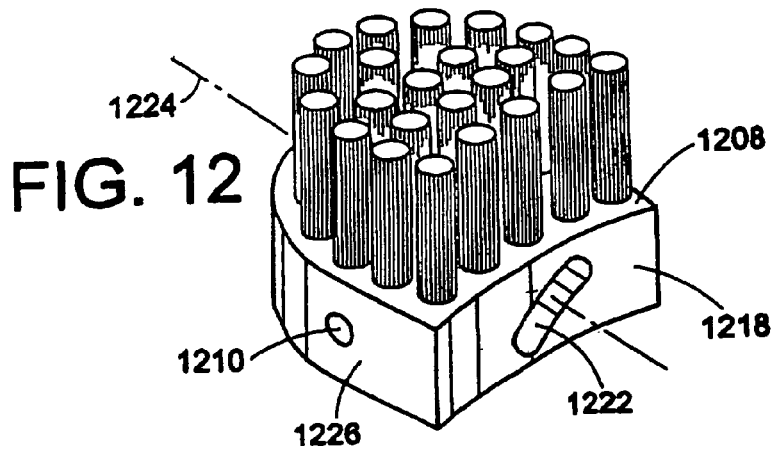
FIG. 12 is an orthographic view of a second bristle holder of a fourth embodiment of a head portion of the enhanced toothbrush of FIG.8.
Figure 13:
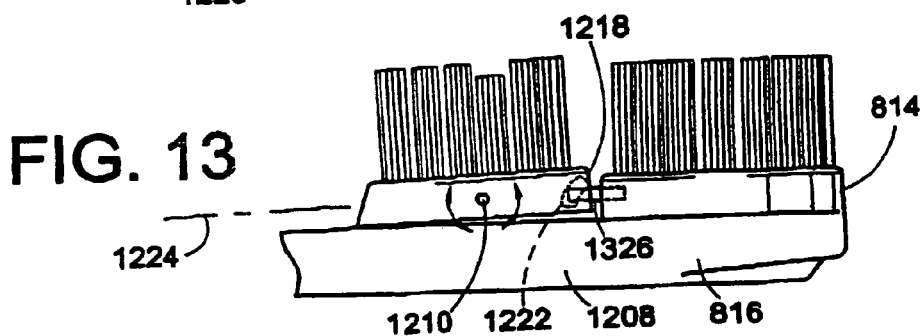
FIG. 13 is a side view, taken along A-A of FIG. 8, in partial section of the fourth embodiment of a head portion of the enhanced toothbrush of FIG.8.

Referring to FIG. 12 and FIG. 13, in a fourth embodiment of the enhanced toothbrush 810, a second bristle holder 1208 is movably mounted to the toothbrush head 816 with a pivot 1210 installed at a centrally located transverse axis of the second bristle holder 1208. The second bristle holder 1208 is driven in a vibratory, swinging or teetering motion by the first bristle holder 814. The second bristle holder 1208 is longitudinally spaced from the first bristle holder 814. A first side 1218 of the second bristle holder 1208 faces the first bristle holder 814. The first side 1218 includes a slot 1222. The slot is disposed transversely to a longitudinal axis 1224 of the second bristle holder 1208 and is oriented at an angle to a plane defined by a base 1226 of the second bristle holder 1208. A pin 1326 interconnects the first bristle holder 814 with the second bristle holder 1208. Preferably, the pin 1326 is molded into, and unitary with, the first bristle holder 814. The pin 1326 is rigidly mounted to or within the first 814 bristle holder. That is to say, the pin 1326 does not move significantly with respect to the first bristle holder. Therefore, the pin 1326 does not constitute an additional moving part. The pin 1326 is received in the angled slot 1222 in the second bristle holder 1208. The slot 1222 is sized to allow the pin 1326 to slide and swing relative to the slot and to engage portions of walls of the slot. As the motor 819 of the enhanced toothbrush 810 rotates the shaft 820, a remote-most end or cam of the shaft 820 (not shown, but similar to 20 of FIG. 3) drives the first bristle holder into rotational or pivotal oscillatory or vibratory motion as described above in reference to FIG. 1-FIG. 7. As the first bristle holder 814 vibrates, the pin 1326 associated therewith, sweeps out an arc. As the pin 1326 sweeps out the arc in a first direction, the pin 1326 engages a first or for example, upper wall of the slot 1222 and urges the first wall, and therefore the second bristle holder, to move in the first or for example, upward (relative to the figure) direction. Since the movement of the second bristle holder is constrained by the pivot 1210, the second bristle holder 1110 is made to swing, teeter or rotate about the pivot 1210 in the first, or for example, upward direction. As the shaft 820 continues to rotate, the first bristle holder is made to move in a second direction. Therefore the pin 1326 is made to sweep out an arc in the second direction. As the pin 1326 sweeps out the arc in the second direction, the pin 1326 engages a second, or for example, lower (relative to the figure) wall of the slot 1222 and urges the second wall, and therefore the second bristle holder 1208 to move in the second, or for example, lower, direction (relative to the figure). Since the movement of the second bristle holder is constrained by the pivot 1210, the second bristle holder 1208 is made to swing, rotate, or teeter about the pivot 1210 in the second direction. As this swinging, pivoting or teetering motion is repeated (as the shaft 820 continues to rotate), a flossing or deep cleaning motion is provided that is distinct from, and complimentary to, the oscillating motion provided by the first bristle holder 814.

Figure 14:
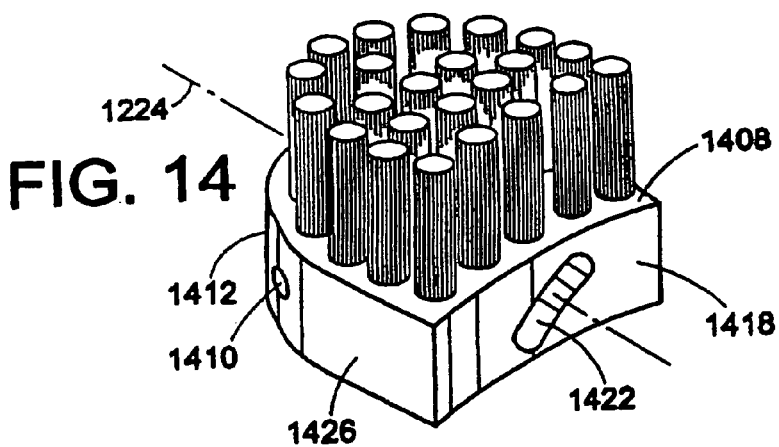
FIG. 14 is an orthographic view of a second bristle holder of a fifth embodiment of a head portion of the enhanced toothbrush of FIG.8.
Figure 15:
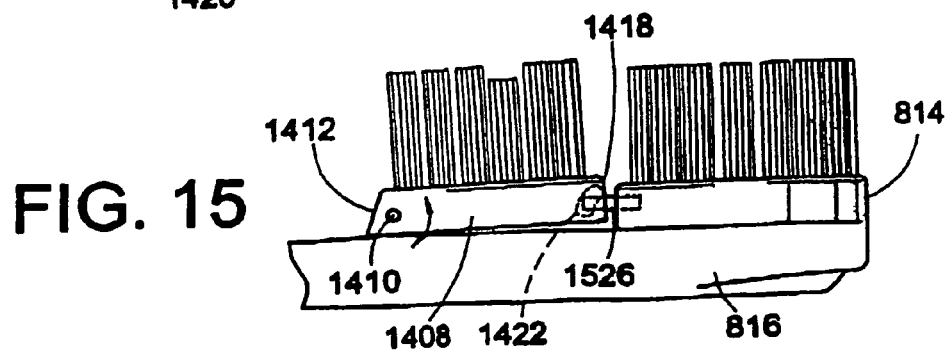
FIG. 15 is a side view, taken along A-A of FIG. 8, in partial section of the fifth embodiment of a head portion of the enhanced toothbrush of FIG.8.

Referring to FIG. 14 and FIG. 15, in a fifth embodiment of the enhanced toothbrush 810, a second bristle holder 1408 is movably mounted to the toothbrush head 816 with a pivot 1410 installed at a transverse axis of the second bristle holder 1408 located adjacent to a proximal end 1412 of the second bristle holder 1410. The second bristle holder 1408 is driven in a vibratory, swinging or teetering motion by the first bristle holder 814. The second bristle holder 1408 is longitudinally spaced from the first bristle holder 814. A first side 1418 of the second bristle holder 1408 faces the first bristle holder 814. The first side 1418 includes a slot 1422. The slot is disposed transversely to a longitudinal axis 1424 of the second bristle holder 1408 and is oriented at an angle to a plane defined by a base 1426 of the second bristle holder 1408. A pin 1526 interconnects the first bristle holder 814 with the second bristle holder 1408. Preferably, the pin 1526 is molded into, and unitary with, the first bristle holder 814. The pin 1526 is rigidly mounted to or within the first 814 holders. That is to say, the pin 1526 does not move significantly with respect to the first bristle holders. Therefore, the pin 1526 does not constitute an additional moving part. The pin 1326 is received in the angled slot 1422 in the second bristle holder 1208. The slot 1422 is sized to allow the pin 1526 to slide and swing relative to the slot and to engage portions of walls of the slot. As the motor 819 of the enhanced toothbrush 810 rotates the shaft 820, a remote-most cam (not shown, but similar to 20 of FIG. 3) of the shaft 820 drives the first bristle 814 holder into rotational or pivotal vibratory motion as described above in reference to FIG. 1-FIG. 7. As the first bristle holder 814 vibrates, the pin 1526 associated therewith, sweeps out an arc. As the pin 1526 sweeps out the arc in a first direction, the pin 1526 engages a first or, for example, upper wall of the slot 1222 and urges the first wall, and therefore the second bristle holder, to move in a first, or for example, an upward (relative to the figure) direction. Since the movement of the second bristle holder is constrained by the pivot 1410, the second bristle holder 1110 is made to swing, or orbit about the pivot 1410 in the first, or for example, upward direction. As the shaft 820 continues to rotate, the first bristle holder is made to move in a second direction. Therefore the pin 1526 is made to sweep out an arc in a second direction. As the pin 1526 sweeps out the arc in the second direction, the pin 1326 engages a second, or for example, lower (relative to the figure) wall of the slot 1422 and urges the second wall, and therefore the second bristle holder 1408 to move in the second, or for example, lower, direction. Since the movement of the second bristle holder is constrained by the pivot 1410, the second bristle holder 1408 is made to swing, or orbit about the pivot 1410 in the second direction. As this swinging, or orbiting motion is repeated (as the shaft 820 continues to rotate), a flossing or deep cleaning motion is provided that is distinct from, and complimentary to, the oscillating motion provided by the first bristle holder 814.

Figure 16:
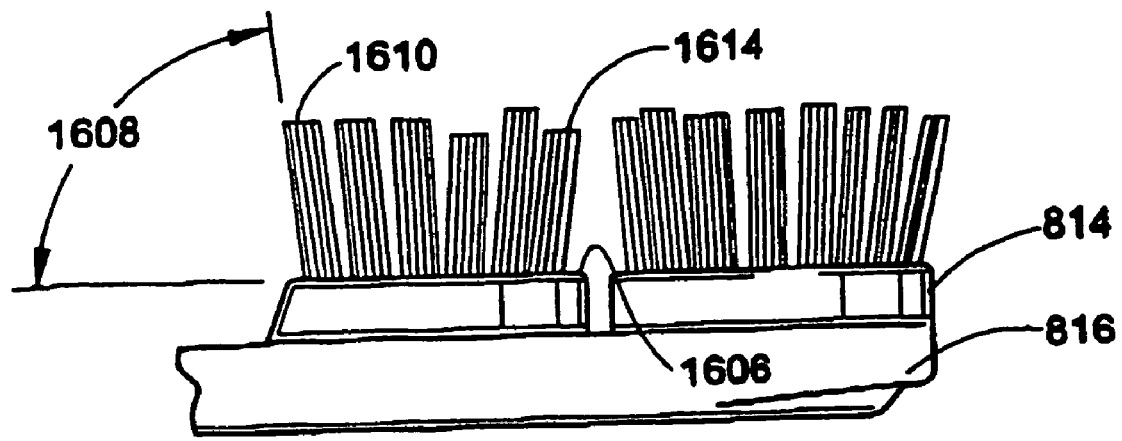
FIG. 16 is a side view of a toothbrush showing a first exemplary alternate bristle arrangement.
Figure 17:
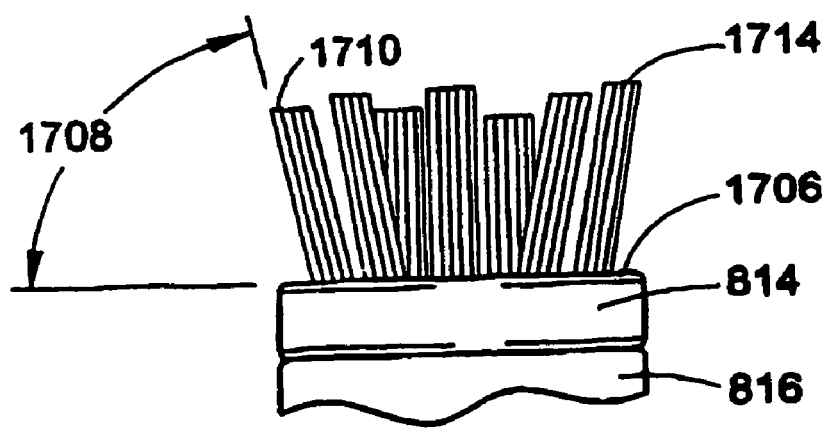
FIG. 17 is an end view taken along D-D of FIG. 8 showing a second exemplary bristle arrangement.

While the embodiments of the present invention have been illustrated for simplicity with bristles, which extend in a direction substantially perpendicular to the longitudinal axis 818 and the surface of the bristle holders, it is contemplated that the bristles might be arranged differently to complement or further enhance the motions of the first and/or second bristle holders. For example, referring to FIG. 16, some or all of the bristles might extend in a direction which forms an acute angle 1608 to a surface 1606 of the bristle holder and extends in a direction toward or away from the handle, such as shown by way of example with respect to bristles 1610 and 1614 respectively. Referring to FIG. 17, in another embodiment, some of the bristles might extend outwardly away from head, in another direction, again forming an acute angle 1708 with respect to the surface 1706 of the bristle holder, as shown by way of example with respect to bristles 1710 and 1714. Massaging bristles or bristles of varying height might also be used, such as described in U.S Pat. Nos. Des. 330,286, Des.

434,563, the substances of which are incorporated herein by reference. Other preferred bristle arrangements suitable for use include those arrangements described in whole or part in U.S Pat. Nos. 6,006,394; 4,081,876; 5,046,213; 5,335,389; 5,392,483; 5,446,940; 4,894,880; and international publication No. WO 99/23910; the substances of which are incorporated herein by reference.

The described embodiments have been described with certain words and phrases that attempt to describe certain motions. Motion can either be constant or vibratory. One example of a constant motion is simple rotation where an element angularly moves in a single direction (e.g., a bristle holder which only rotates clockwise or swivels clockwise in a cone like envelope) or translates in a single direction. Vibration is any periodic movement having repeated cycles. Vibratory motion can have one or more frequencies and amplitudes. Vibratory movement which is substantially linear is referred to herein as a reciprocating motion. Reciprocating motion can occur in a number of directions, such as substantially horizontal, substantially vertical (i.e., a lifting or pulsating motion), and combinations thereof. Vibratory movement which is substantially rotational in nature is referred to herein as an oscillatory or pivoting motion.

Because most motions can be complex in nature (i.e., include elements of other types of motion), the use of the above-described terms herein can include other motions, unless stated otherwise (e.g., reciprocates only), in addition to the basic or primary motion described by the term. So, for example, a motion which is described herein as reciprocating may also include other vibratory or constant movements even though the primary movement is reciprocatory in nature.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The invention has been described with reference to particular embodiments. Modifications and alterations will occur to others upon reading and understanding this specification. For example, while the first bristle holder has been described and illustrated as being adjacent a remote-most end of the toothbrush and the second bristle holder as being located more proximally, the two holders may be switched in position. For example, the first, or driven, bristle holder may be located proximally while the second or slave bristle holder is located at the remote or more distal end of the toothbrush. While the pins have been described as being molded unitary components of the first bristle holder, the pins may comprise separately manufactured and subsequently fixedly attached, inserted or co-molded components. It is intended that all such modifications and alterations are included insofar as they come within the scope of the appended claims or equivalents thereof.

What is claimed is:

1. An electric toothbrush, comprising:
a handle at a first end of the toothbrush;
a head at a second end of the toothbrush, the head having a longitudinal axis and comprising a first bristle holder having a first plurality of bristle tufts, and a second bristle holder having a second plurality of bristle tufts;
a drive system comprising a motor and a rotatable shaft, wherein the rotatable shaft extends from the motor and into the head;
wherein the first bristle holder oscillates about a first axis, wherein a protrusion extends from the first bristle holder;
wherein the second bristle holder is operatively connected to the first bristle holder via the protrusion;
wherein the second bristle holder is located between the first bristle holder and the handle;
wherein the second bristle holder is driven by the first bristle holder;
wherein the second bristle holder oscillates about a second axis; and
wherein the second axis does not intersect the first bristle holder.

2. The electric toothbrush of claim 1, wherein the protrusion is received by a slot of the second bristle holder.

3. The electric toothbrush of claim 1, wherein the second bristle holder is biased by a spring.

4. The electric toothbrush of claim 1, wherein the second bristle holder comprises a second protrusion, wherein the second bristle holder is driven by camming action of the second protrusion and the protrusion of the first bristle holder.

5. The electric toothbrush of claim 1, wherein a first portion of the plurality of bristle tufts of the first bristle holder is shorter than a second portion of the plurality of bristle tufts of the first bristle holder.

6. The electric toothbrush of claim 5, wherein a first portion of the second plurality of bristle tufts of the second bristle holder is shorter than a second portion of the second plurality of bristle tufts of the second bristle holder.

7. The electric toothbrush of claim 1, wherein the protrusion is unitary with the first bristle holder.

8. The electric toothbrush of claim 1, wherein the protrusion is rigidly connected to the first bristle holder.

9. The electric toothbrush of claim 1, wherein the second bristle holder reciprocates along a second axis generally transverse to the first axis.

10. The electric toothbrush of claim 9, wherein the second axis is generally parallel to the longitudinal axis.

11. The electric toothbrush of claim 1, wherein the protrusion remains substantially stationary relative to the first bristle holder.

12. The electric toothbrush of claim 1, wherein the shaft is operatively connected to the first bristle holder.

13. The electric toothbrush of claim 1, wherein the protrusion extends in a direction perpendicular to the first axis.

14. The electric toothbrush of claim 1, wherein the protrusion is a pin.

* * * * *